United States Patent [19]

Landaburu et al.

[11] Patent Number: 4,585,654
[45] Date of Patent: Apr. 29, 1986

[54] PROCESS FOR PASTEURIZING FIBRONECTIN

[75] Inventors: Ricardo H. Landaburu, Rye Town, N.Y.; Godfrey W. Amphlett, Boston, Mass.; Roy E. Branson, San Ramon, Calif.; Arthur B. Shaw, Harrison, N.Y.

[73] Assignee: Armour Pharmaceutical Co., Tarrytown, N.Y.

[21] Appl. No.: 684,440

[22] Filed: Dec. 21, 1984

Related U.S. Application Data

[63] Continuation-in-part of Ser. No. 489,886, Apr. 29, 1983, abandoned.

[51] Int. Cl.$^4$ .................. A61K 37/02; A61K 35/14
[52] U.S. Cl. ........................... 424/101; 514/2; 514/21; 422/1
[58] Field of Search ............... 424/101; 514/21, 2, 514/802

[56] References Cited

U.S. PATENT DOCUMENTS

| | | | |
|---|---|---|---|
| 4,314,997 | 4/1982 | Fukushima | 424/101 |
| 4,327,086 | 2/1982 | Shanbrom | 424/101 |
| 4,404,187 | 9/1983 | Schwinn et al. | 424/101 |

FOREIGN PATENT DOCUMENTS

| | | | |
|---|---|---|---|
| 0058993 | 1/1982 | European Pat. Off. | 424/177 |
| 3033932 | 9/1980 | Fed. Rep. of Germany | 514/21 |

Primary Examiner—Donald B. Moyer
Assistant Examiner—Jacqueline M. Stone

[57] ABSTRACT

A process for heating and simultaneously agitating a plasma protein solution in the presence of a polyol, a surface active agent and a chelating agent. Said process inactivates viruses in said solution while preserving the physical and biological properties of said plasma protein.

2 Claims, No Drawings

PROCESS FOR PASTEURIZING FIBRONECTIN

BACKGROUND OF THE INVENTION

This application is a continuation in part of application Ser. No. 489,886 filed Apr. 29, 1983, now abandoned.

1. Field of the Invention

This invention relates to rendering fibronectin free of transmissible biological contaminants such as viruses and the like, and especially infectious hepatitis viruses, such as hepatitis virus B, and the Non-A, Non-B infectious virus(es).

Fibronectin is a large complex protein possessing important biological functions such as acting as a structural component of tissues and modulating the function of cells in the body. Its actions include control of normal growth, participation in the repair of damage, and involvement in defense against invading foreign substances and organisms. It is known by a variety of names that reflect its diverse biological activities including the names of: large external transformation sensitive protein (LETS); cell surface protein (CSP); cell adhesion protein (CAP); opsonic α2 surface binding glycoprotein; and cold insoluble globulin (CIG). Pharmacological application of fibronectin includes treatment of septic shock and infective diseases. Due to its action of enhancing intercellular adhesive properties and its effect on the morphology of cancer cells, it is a potential candidate for cancer treatment.

(Considerable interest is expressed in fibronectin by the scientific community. For Example:

*The American Journal of Dermatopathology* Vol. 4, No. 2, pp. 185–188 (April 1982);

Science, Vol. 201, pp. 622–624, (August 1978);

*Journal of the Reticuloendothelial Society,* Vol. 22, pp. 583–596 (December 1977); and

*Annals of Surgery,* Vol. 188, No. 4, pp. 521–529 (October 1978).)

Fibronectin is obtained from fractions of plasma protein or fibroblast culture fluid. Contamination by viruses may result from both the source material used and from the environment during the separation procedure.

Although efforts are being made to utilize plasma which is negative to hepatitis virus B, when tested using high sensitivity methods such as radioimmunoassay or passive hemagglutination, the danger of such contamination still exists because the presence of the virus cannot be detected with certainty by any known procedure. In addition, there are no available in vitro test methods to detect the Non-A, Non-B Hepatitis virus(es).

To be suitable for clinical application, fibronectin must be free of contaminants, especially infectious hepatitis viruses, it must possess a high degree of therapeutic activity, and it must have a good shelf-life.

Attempts have been made to deactivate viruses in plasma proteins by heat treatment at temperatures ranging from 1° to 50° C. While some viruses may be deactivated by such treatment, it is generally accepted that deactivation of infectious hepatitis viruses requires heat treatment for about 10 hours at about 60° C. The problem confronting the prior art is the thermal instability of fibronectin: heat treatment above 40°–45° C. causes coagulation, denaturation and loss of activity therein.

2. Description of the Prior Art

It has been known for many years that certain polyols confer heat stability to proteins against denaturation during pasteurization sufficient to render hepatitis virus inactive. Such polyols include polyhydric alcohols and carbohydrates, such as arabinose, glucose, galactose, fructose, ribose, mannose, rhomnose, sucrose, maltose, raffinose, and the like.

Fibronectin has also been stabilized during or prior to pasteurization by certain sugars, such as sucrose, and by the use of certain sugars in conjunction with some other stabilizing agents, such as neutral amino acids, hydrocarbon carboxylic acids, and hydroxyhydrocarbon carboxylic acids.

While inactivation of infectious hepatitis viruses has been adequately attained and heat stability of proteins in general was markedly increased, the native character of such proteins has not been sufficiently preserved from denaturation. This lack of complete preservation of physical and biological activity is especially apparent in large scale production of proteins such as fibronectin. As opposed to the mechanically static conditions of laboratory scale procedures wherein, as a result of large surface area to small volume ratio, effective transfer of heat into the solution is easily attained without mechanical agitation, in large scale manufacturing procedures the surface to volume ratio of the liquid being processed is drastically reduced and extensive mechanical agitation is necessary to effect uniform temperature therein. It has been observed that when heat and mechanical agitation are applied simultaneously during pasteurization, carbohydrates will not fully protect fibronectin from denaturation and loss of yield. Such denaturation is apparent during the pasteurization process as fibronectin coagulates and adheres to the surfaces of the pasteurizing apparatus. It has also been found that in large scale manufacturing operations, in addition to the denaturing forces of heat and mechanical stress, polymeric forms of fibronectin are generated as a consequence of the catalyzing action of certain metal ions which may be present in the solution being processed or in the sterilizing equipment used from which they leach out into the solution from such objects as vessel walls, valves and surfaces of the operating equipment of metal and nonmetal construction. An example of such an undesirable metal ion is $Cu^{2+}$ which causes polymerization of fibronectin via disulfide formation through a free sulfhydryl group in the fibronectin molecule. The presence of even a minute amount of metal ions is sufficient to cause the undesired polymerization of fibronectin during the prolonged heating and agitation.

Accordingly, it is an object of the present invention to provide fibronectin and other proteins rendered free of infectious hepatitis viruses.

It is another object of the present invention to pasteurize fibronectin and other proteins without causing denaturation thereto.

It is still another object of the present invention to pasteurize fibronectin and other proteins without forming polymerized forms of such fibronectins and other proteins.

It is a further object of the present invention to provide a simple large scale pasteurizing process for fibronectin and other proteins observing and utilizing the art-recognized conditions of heating the protein solution for about 10 hours at about 60° C. to assure safety from contaminating viruses.

While the present invention will be described with reference to fibronectin, the pasteurizing/stabilizing procedures are also applicable to proteins other than fibronectin behaving similarly to fibronectin.

SUMMARY OF THE INVENTION

According to the present invention, it has been found that the native character and biological properties of fibronectin may be preserved during an effective pasteurization procedure against viruses and without the formation of undesirable polymeric forms of fibronectin by utilizing in the aqueous solution containing fibronectin: a heat stability conferring polyol; a surface active agent which by the properties conferred on the solvent and its interaction with fibronectin diminishes the mechanical denaturing stresses resulting from agitation; and a chelating agent to sequester and render inactive, polymerization catalyzing trace metals present in the fibronectin solution or in the sterilizing apparatus.

Thus the present invention encompasses the process of heat treatment to inactivate viruses of an aqueous solution containing a plasma protein, such as fibronectin, comprising:

heating and simultaneously mechanically agitating, such as stirring and shaking, said plasma protein solution at about 60° to 70° C. for about 10 to 20 hours to effect pasteurization thereof in the presence of: 25% to 50% w/v of a polyol selected from the group consisting of sucrose, maltose, lactose, glucose, mannose, and galactose; 0.01% to 0.5% w/v of a surface active agent selected from the group consisting of polyoxyethylene sorbitan mono- and tri- esters, sodium cholate, sodium taurocholate, sodium deoxycholate, and sodium glycocholate; and 0.0005 to 0.2M of a chelating agent selected from the group consisting of ethylenediaminetetraacetic acid, ethylene-bis-oxyethylene nitrile and orthophenanthrolene.

In general, to the aqueous solution containing fibronectin, appropriate amounts of polyol, surface active and chelating agents are added forming a suspension which is then heated for 10 to 20 hours at about 60°-70° C. After pasteurization the viscous suspension is diluted and filtered through ion exchange columns or ligand-affinity columns to remove the additives and non-specifically bound proteins. The pure fibronectin is then formulated into appropriate dosages.

DETAILED DESCRIPTION OF THE INVENTION

In accordance with the present invention, fibronectin is pasteurized in the presence of a polyol, a surface active agent and a chelating agent, the combined effect of which insures that fibronectin is preserved in its native form during the heating and simultaneous agitating process.

The heat treatment is carried out at a temperature and for a period of time which are sufficient to inactivate the viruses, especially infectious viruses such as hepatitis viruses, but at the same time to retain the activity of fibronectin. Such heat treatment and simultaneous agitation is maintained for about 10 to 20 hours at about 60°-70° C., and preferably at 60oC for 10 hours.

Fibronectin

Fibronectin is well known in the prior art. It is available from commercial sources such as: Sigma, St. Louis, MO.; Calbiochem, La Jolla, CA.; Bethesda Res. Lab., MD.; California Biomedical Co. and Meloy Lab., Springfield, VA. Methods of preparing and/or purifying fibronectin are also known, for example, (A) *Analytical Biochem.* 79, 144–151 (1977), and (B) *Biochem, J.*, 183, 331–337 (1979).

For the purposes of the present invention, in addition to using a purified fibronectin, various starting solutions of fibronectin may be used, including impure forms of fibronectin such as human plasma, cryoprecipitate, the Acid-Chill Precipitate obtained from cryoprecipitate which is analogous to Fraction I-O, or Fraction I. While, as indicated, the aqueous solution containing fibronectin to be used as starting material in the present invention may be in any stage of purification ranging from purified to unpurified aqueous solution, we prefer to use at least a partially purified aqueous fibronectin.

Polyols

In the present invention we prefer to use the disaccharide sucrose (saccharose) as the preferred agent for conferring heat stability to fibronectin during pasteurization. We have found that a concentration range of about 25 to 60% w/v is effective for such stabilization, with the preferred concentration being about 30% to 50% w/v. While on the one hand, even lower concentrations might be used for the stabilization, the yield of fibronectin tends to be affected at such lower concentration, and on the other hand, higher than the stated concentration limit will deleteriously affect subsequent processing of the pasteurized solution due to the high viscosity property rendered thereto by the large amounts of sugar present.

Other polyols may be substituted for the disaccharide sucrose, such as: other disaccharides, such as maltose and lactose; monosaccharides, such as glucose, galactose and mannose; certain polyhydric alcohols, such as glycerol; and certain polymers such as polyethylene glycol.

Surface Active Agents

Surface active agents used to advantage in accordance with the present invention must have the criteria of pharmaceutical acceptability and capability of easy removal from the solution after pasteurization thereof. A small quantity of these surface active agents was found to be effective to provide stability to fibronectin when used in conjunction with a polyol which is unable to prevent at least a partial loss due to denaturation and polymerization of fibronectin due to the combination of heat treatment and mechanical agitation. It was found that the use of pharmaceutically acceptable surface active agents in a concentration range of about 0.01% to 0.5% w/v is sufficient to lend the protective effect to the fibronectin, while a concentraction range of about 0.02% to 0.10% w/v is preferred. It was further found that even though higher quantities of particular surface active agents would perform satisfactorily, the use of excessive amounts of same is undesirable for reason of difficulty encountered with removal thereof from the pasteurized solution.

It was found that poly(oxy-alkylene) mono- and tri-sorbitan esters (fatty acid esters of sorbitol and its anhydrides copolymerized with a varying number of moles of ethylene oxide), are well suited as surface active agents for the purposes of the present invention, such as Polysorbate 80 (an oleate ester), Polysorbate 20 (a laurate ester), Polysorbate 40 (a palmitate ester), and Polysorbate 60 (a stearate ester).

Other surface active agents useful in the present invention include nonionic agents such as alkyl phenyl polyoxyethylenes (such as Triton ® and Nonidet ®);

anionic agents such as the bile salts (sodium taurocholate, sodium cholate, sodium deoxycholate and sodium glycocholate); cationic agents such as benzalkonium chloride; and polyhydric alcohols with surface active properties such as the high molecular weight copolymers of propylene glycol and propylene oxide sold under the trade names of Pluronic ® F-38 and Pluronic ® F-68.

Chelating Agents

As previously indicated, in addition to the denaturing forces of heat and mechanical stress, a catalytic chemical action can contribute to the denaturation of the protein being sterilized. Heat and agitation tend to accelerate such catalytic chemical action resulting in the formation of polymeric forms of fibronectin. Trace quantities of certain metal ions, such as $Cu^{2+}$, are sufficient to cause such an undesired result. It is believed that $Cu^{2+}$ ion causes polymerization of fibronectin via disulfide formation through a free sulfhydryl group in the fibronectin molecule. Other metal ions known to be reactive with the sulfyhydryl moieties of proteins may cause similar activity or simply form insoluble sulfide salts. Whereas these metal ions may not, per se, be present in the solution of protein being pasteurized, such may leach into the solution from vessel walls, valves and various surfaces of the pasteurizing apparatus. To sequester these metal ions a chelating agent is used in the range of about 0.0005 to 0.2 molar and preferably in the range of about 0.001 to 0.01 molar, such as ethylenediaminetetraacetic acid (EDTA), ethylene-bis-oxyethylenenitrile thetraacetic acid (EGTA), and orthophenanthrolene. Other chelating agents which are easily separated from the solution upon completion of pasteurization are also in the purview of the present invention.

In combination with chelating agents, a buffer solution may also be employed to sequester trace metal ions, such as a sodium citrate buffer in 0.0005 to 0.2 molar concentration range.

An alternative method for preventing the oxidation of the sulfhydryls may be the addition of 0.0005 to 0.2 molar of directly-acting antioxidants, such as ascorbic acid or cysteine.

The invention will be illustrated in more detail with reference to the following examples.

EXAMPLE 1

5 kg Fraction I-0 derived from cryoprecipitate was resuspended and dissolved in 3 volumes of sodium chloride (0.15M), buffered with sodium citrate (0.01M) and glycine (0.05M) (hereinafter cgs buffer) at pH 7.3, by warming the solution at 37° C. with gentle stirring. The solution was clarified by ordinary filtration on non-fiber releasing media such as Zetapor ® (AMF Cuno) with a diatomaceous earth filter-aid coating. The resultant solution was diluted with approximately 20 volumes of the same buffer with concurrent addition of sufficient sucrose to make the final solution 50% w/v, Polysorbate 80 was added to obtain a concentration of 0.05% w/v followed by the addition of sufficient EDTA to make the final solution 0.005M.

With vigorous mechanical agitation the solution of fibronectin in the impure form and comprising 115 liters was heated in a stainless steel tank of 50 gallon capacity with an integral heat exchange surface so as to achieve a temperature of 60° C. in a period of one to four hours. On achieving an internally recorded solution temperature of 59.5° C., the solution was held with agitation continued for 10 hours at 60°±0.5° C. It was then diluted with a chilled pasteurization medium, from which sucrose has been omitted, to a volume of about 230 liters, so as to effect the lowering of temperature to about 20°–45° C. At this stage a considerable precipitate in the form of denatured protein, which does not include fibronectin, will have formed as the result of the prolonged heating, and this was removed from the solution by ordinary filtration on media such as Zetapor ® using a diatomaceous earth filter aid.

The filtrate from this process was retained at a temperature of about 20° C. to 40° C. until further purification was effected.

EXAMPLE 2

Ten liters of human plasma, from which antihemophilic factor has been removed without loss of the majority of the fibronectin present in the native plasma, was adjusted to contain 50% sucrose (w/v) of final solution in the final volume of 20 liters. The solution was made 0.01M in sodium citrate, 0.05M in glycine, and 0.005M in EDTA without adjustment to the anticoagulant present during plasma collection. Polysorbate 80 was added to obtain a final concentration of 0.05% w/v. The pH was adjusted to between 7.0 and 7.4. The resultant solution was heated with vigorous agitation in a stainless steel vessel of 15 gallon capacity, which contains an integral heat exchanger surface, so that a temperature of 60° C.±0.5° C. was reached in one to four hours. With continuous agitation, this temperature was maintained for a period of 10 hours. This solution was then diluted two-fold with chilled pasteurization medium from which sucrose has been omitted so as to effect lowering the temperature to about 20°–45° C. Denatured protein which does not include the desired fibronectin remains in suspension, and this is removed by ordinary filtration on media such as Zatapor ® using a diatomaceous earth filter aid.

EXAMPLE 3

5 kg of Acid-Chill Precipitate obtained from human plasma is resuspended and dissolved in 3 volumes of cgs buffer at pH 7.3, by warming the solution at 37° C. with gentle stirring. The solution was clarified by ordinary filtration on non-fiber releasing media such as Zetapor ® (AMF Cuno) with a diatomaceous earth filter-aid coating. The resultant solution was diluted with approximately 20 volumes of the same buffer with concurrent addition of sufficient sucrose to make the final solution 50% w/v, Polysorbate 80 was added to obtain a concentration of 0.05% w/v followed by the addition of sufficient EDTA to make the final solution 0.005M.

With vigorous methanical agitation the solution of fibronectin in the impure form and comprising 80 liters was heated in a stainless steel tank of 25 gallon capacity with an integral heat exchange surface so as to achieve a temperature of 60° C. in a period of one to four hours. On achieving an internally recorded solution temperature of 59.5° C., the solution was held with agitation continued for 10 hours at 60°±0.5° C. It was then diluted with a chilled pasteurization medium, from which sucrose has been omitted, to a volume of about 160 liters, so as to effect the lowering of temperature to about 20°–45° C. At this stage a considerable precipitate in the form of denatured protein, which does not include fibronectin, will have formed as the result of the prolonged heating, and this is removed from the solution by ordinary filtration on media such as Zetapor ®️ using a diatomaceous earth filter aid.

The filtrate from this process was cooled to 5° C. (±2° C.) and retained at this temperature until further purification was effected.

Next, the filtrate is warmed to 22° C. and then applied at a flow rate of 20 ml/cm$_2$/hr to a Sepharos ®️-gelatin column that has been previously prepared by the cyanogen bromide activation method, followed by washing with deionized 8M urea in cgs buffer. Then the column containing fibronectin bound to the Sepharose ®️-gelatin was washed with 1M deionized urea in cgs buffer. In this step EDTA, Tween 80, sucrose and non-specifically bound proteins are removed.

Next, the fibronectin was eluted from the Sepharose ®️-gelatin with a solution of 8M urea in cgs buffer. The urea was removed from the fibronectin by passing the eluted fibronectin through a G-25 Sephadex ®️ column that was previously equilibrated with a solution containing 0.05M NaCl and 2 mM sodium citrate at a pH of 7.3.

The so obtained fibronectin solution was made into formulations and sterile filtered.

A set of experiments using purified, unpasteurized fibronectin was performed to examine the effects of heat and agitation for varying periods of time on the properties of fibronectin. The experiments and results thereof are described in the examples that follow.

EXAMPLE 4

This example demonstrates the agitation-induced presipitation effect on fibronectin. Aqueous buffered solutions of fibronectin (1 mg/ml) having adducts indicated below were agitated on a wrist action shaker at 25° C. for 30 minutes. A fibrous white precipitate was visible in the samples denoted with (+). The protein lost from the solution was assayed by measuring the optical density of the remaining clear colution at 280 nm and comparing it with a control

| Additions to 1 mg/ml Fibronectin Solution (w/v) | Formation of Fibrous White Precipitate | Percent Protein Lost |
| --- | --- | --- |
| None | + | 1 |
| 50% Sucrose | + | 46 |
| 0.05% Tween 80 ®️ | − | 0 |
| 50% Sucrose + 0.05% Tween 80 ®️ | − | 0 |

EXAMPLE 5

This example demonstrates the heat-induced denaturation effect.

Aqueous buffered solution of fibronectin (1 mg/ml) having adducts indicated below were heated without agitation for 30 minutes at 60° C. Following dialysis against buffer, the samples were tested as follows.

(a) Gelatin Binding Activity (assayed by a method analogous to that of Engvall et al., *J. Exp. Med.* 147, 1584 (1978))

| Additions to 1 mg/ml Fibronectin Solution (w/v) | Percent Loss in Gelatin Binding Activity Compared with Unheated Control |
| --- | --- |
| None | 36.5 |
| 50% Sucrose | 18.7 |
| 0.05% Tween 80 ®️ | 25.3 |
| 50% Sucrose + 0.05% Tween 80 ®️ | 0 |

(b) Aggregates Detected by SDS Gel Electrophoresis.

| Additions to 1 mg/ml Fibronectin Solution (w/v) | Precent of Protein with Molecular Weight Greater then 440,000 Daltons |
| --- | --- |
| None | 53 |
| 50% Sucrose | 15 |
| 0.05% Tween 80 ®️ | 63 |
| 50% Sucrose + 0.05% Tween 80 ®️ | 15 |
| Unheated Control | 19 |

(c) Fluorescence Emission Spectrum

| Additions to 1 mg/ml Fibronectin Solution (w/v) | Shift in Emmission Spectrum Relative to Unheated Control, nm |
| --- | --- |
| None | +3.5 |
| 50% Sucrose | 0 |
| 0.05% Tween 80 ®️ | +4.5 |
| 50% Sucrose + 0.05% Tween 80 ®️ | 0 |

EXAMPLE 6

This example demonstrates both the heat induced denaturation and agitation-induced precipitation effects on fibronectin.

The producure of Example 4 was repeated as described therein, except the agitation continued for 10 hours at 58°-60° C.

| Additions to 1 mg/ml Fibronectin Solution (w/v) | Formation of Fibrous White Precipitate | Percent Protein Lost | Percent Loss in Gelatin Binding Compared with Unheated Control |
| --- | --- | --- | --- |
| 50% Sucrose | + | 36 | 36 |
| 0.05% Tween 80 ®️ | − | 0 | 100 |
| 50% Sucrose + 0.05% Tween 80 ®️ | − | 0 | 0 |

As can be easily ascetained from the above examples the combination of a sugar and surfactant is necessary to prevent both the agitation-induced precipitation effect and the heat-induced denaturation effect when the fibronectin solution is pasteurized by heat and agitation; neither a sugar nor a surfactant alone prevents both effects.

EXAMPLE 7

This example demonstrates the metal-ion induced aggregation of fibronectin. Solutions of fibronectin (5 mg/ml in cgs buffer) having adducts indicated below were dialyzed against buffered solutions (0.05M Tris-HCl, 0.1 M NaCl, pH 7.4) containing the same adducts for 24 hours at 25° C. The extent of aggregation was measured by SDS polyacrylamide gel electrophoresis.

| Additions to Fibronectin and Dialysis Buffer | Percent of Protein on SDS Polyacrylamide Gel with Molecular Weight Greater than 440,000 Daltons |
|---|---|
| None | 5 |
| 0.1 mM CuCl$_2$ | 20 |
| 0.1 mM CuCl$_2$ + 5 mM EDTA | 2 |

EXAMPLE 8

This example further demonstrates that only the combination of ingredients, namely a carbohydrate, chelating agent and surface active agent, is capable of preserving the fibronectin from denaturation during the pasteurization via heating and agitation.

Aqueous buffered solutions of fibronectin containing 1 mg fibronectin/ml of solution having adducts indicated below were agitated throughout the heating process on a wrist action shaker and heated for 10 hours at 60°–62° C.

Using the test procedures described in the specification the following results were obtained:

Effect of heat and Simultaneous Agitation on Fibronectin

| Additions to 1 mg/ml Fibronectin Solution | Formation of Fibrous White Precipitate | Percent Protein Lost | Percent Loss In Gelatin Binding Compared with Unheated Control |
|---|---|---|---|
| No addition (Control) | + | 75 | 100 |
| 0.5 mM EDTA | + | 75 | 100 |
| 50% Sucrose + 0.5 mM EDTA | + | 70 | 43 |
| 0.5% Tween 80 ® + 0.05 mM EDTA | − | 0 | 100 |
| 50% Sucrose + 0.5 mM EDTA + 0.05% Tween 80 ® | − | 0 | 3 |

EXAMPLE 9

This example shows that the product obtained by the process of the present invention is essentially the same as the product known by the prior art.

Affinity Purification of Human Plasma Fibronectin Nonpasteurized (Method A)

Five kilograms of Acid-Chill Precipitate was dissolved in three volumes of 0.15M sodium chloride, 0.05M glycine, 0.01M sodium citrate, pH 7.2+0.2 (cgs buffer) at 37° C. with agitation. After solubilization, Standard Super Cel (filtration aid) was added to a final concentration of 2% weight/volume.

This mixture was stirred for approximately two minutes. This suspension of Standard Super Cel and Acid-Chill Precipitate was then pressure filtered through a series of 60 SP Cuno filter pads. This filtered solution was then loaded by gravity onto a gelatin-Sepharose column at room temperature. After the solution was loaded, the column was washed with 10–15 column volumes of 1M deionized urea in cgs buffer. The fibronectin was eluted from the gelatin-Sepharose column by 8M urea in cgs buffer. The urea was removed from the eluted fibronectin by desalting on Sephadex G-25 column. The fibronectin was desalted into cgs buffer.

Pasteurized (Method B)

Five kilograms of Acid-Chill Precipitate was dissolved in three volumes of cgs buffer at 37° C. with agitation. After solubilization, Standard Super Cel (filtration aid) was added to the final concentration of 2% weight/volume. This mixture was stirred for approximately two minutes. This suspension of Standard Super Cel and Acid-Chill Precipitate was then pressure filtered through a series of 60 SP Cuno filter pads. This filtered solution of crude fibronectin was then made 50% weight/volume with respect to sucrose by the addition of a 77% weight/volume solution of sucrose in cgs buffer. EDTA and TWEEN 80 were then added to a final concentration of 0.005M and 0.05% w/v respectively. This solution of crude fibronectin, sucrose, EDTA and TWEEN 80 was continually agitated while the temperature was raised to 60° C. The solution was maintained at 60°±0.5° C. with constant mixing for 10 hours.

After heating at 60° C. for 10 hours, the crude fibronectin solution was diluted with an equal volume of 0.15M sodium chloride, 0.05M glycine, 0.01M sodium citrate, 0.005M EDTA and 0.05% TWEEN 80 while maintaining the temperature at 40°±0.5° C. Hyflo Super Cel (a filtration aid) was added to a final concentration of 1.5% weight/volume to this crude fibronectin solution. This suspension of fibronectin and Hyflo Super Cel was stirred two minutes and then pressure filtered through a series of 60 SP Cuno filter pads.

This filtered solution of fibronectin was then loaded by gravity onto a gelatin-Sepharose column at room temperature. After the solution has been loaded, the column was washed with 10–15 column volumes of 1M deionized urea in cgs buffer. The fibronectin was eluted from the gelatin-Sepharose column with 8M deionized urea in cgs buffer. The urea was removed from the eluted fibronectin by desalting on a Sephadex G-25 column. The fibronectin was desalted into cgs buffer.

The human plasma fibronectins prepared by these two methods were assayed in vitro for a) their ability to promote cell attachment and b) their ability to enhance the opsonization of target particles for peritoneal macrophages. These assays are described in the following sections.

Human Umbilical Vein Endothelial Cell Attachment Assay

Human umbilical vein endothelial cells were seeded in Medium 199 at a density of $1.25 \times 10^4$ cells/cm$^2$ in duplicate 35mm cell culture dishes that had been pre-coated with various concentrations of pasteurized and nonpasteurized affinity purified human fibronectin (products obtained in Method A and Method B respectively). After ten minutes at 25° C. the medium was aspirated and Medium 199 containing 20% Fetal Bovine Serum and 100 μg/ml endothelial cell growth factor (ECGF) was added to each culture dish. The cells were incubated at 37° C. for two hours at which time the culture dishes were washed twice with Medium 199, the cells were harvested with trypsin-EDTA and duplicate hemocytometer cell counts were obtained. Cell culture dishes that were not treated with human fibronectin served as controls.

Human Umbilical Vein Endothelial Cell Attachment

| μG HFN/Cm² (μg/Cm²) | Pasteurized HFN/HUV END Cells 10⁴ | Non Pasteurized HFN/HUV END Cells 10⁴ |
|---|---|---|
| 1 | 5.1 | 3.7 |
| 5 | 6.4 | 6.7 |
| 10 | 7.1 | 5.6 |
| 20 | 6.3 | 6.3 |

The result indicates that there is essentially no difference between pasteurized and nonpasteurized human plasma fibronectin in their ability to enhance the attachment of human umbilical vein endothelial cells to plastic tissue culture dishes.

In Vitro Opsonization Assay

Fibronectin has a number of biological activities which relate to its physiological role. The most commonly measured activity is the ability to promote the phagocytosis of foreign particles. The following in vitro assay system measures this opsonic activity. The assay measures the fibronectin-mediated uptake of radioactive gelatin-coated latex particles by activated rat macrophages. The procedure is as follows:

Gelatin was convalently attached to 0.45 micron latex beads and radioiodinated to form $^{125}$I-gelatin coated latex beads (gel-ltx).

Male Sprague-Dawley rats (200-250 g) were injected intraperitoneally with 1% casein in phosphate buffered saline. Three days later, macrophages were collected from the peritoneum of the injected rats. The cells were plated in Linbro 24 well tissue culture plates at $1.75 \times 10^6$ cells/well. The medium was Dulbecco's Minimal Eagle Medium containing 50 units/ml of penicillin, 50 μg/ml of streptomycin, and 20% heat-inactivated bovine fetal serum. After 2 hours at 37° C. in 5% $CO_2$ in air, the nonadherent cells were washed off the plate and fresh medium (with bovine serum ablumin replacing the bovine fetal serum) was added. Fibronectin samples prepared by Method A (nonpasteurized) and Method B (pasteurized) (0–100 μg/well) and gel-ltx beads (200 μg/well) were added. The plates were incubated for 2 hours at 37° C. in 5% $CO_2$ in air. The plates were then washed with phosphate buffered saline. The cells were solubilized with 0.1N NaOH. The radioactivity and protein content of each sample were determined. The results are expressed as counts per minute (cpm) per 50 μg of cell protein.

HFN Opsonic Activity

| CPM/50 μg Cell Protein | HFN (μg) Pasteurized | HFN (μg) Nonpasteurized |
|---|---|---|
| 4 | 1,352 | 1,253 |
| 5 | 1,400 | 903 |
| 6 | 1,543 | 863 |
| 7 | 1,707 | 1,833 |
| 8 | 1,651 | 1,719 |
| 10 | 1,650 | 1,552 |
| 12 | 1,922 | 1,873 |
| 15 | 2,006 | 2,079 |
| 20 | 2,532 | 1,850 |
| 100 | 2,684 | 2,660 |

The samples of Method A (nonpasteurized fibronectin) and Method B (pasteurized fibronectin) show essentially the same opsonic activity.

EXAMPLE 10

Peritoneal Macrophage Monolayer Assay

This assay was performed on the pasteurized fibronectin obtained by the process of the present invention and on nonpasteurized (commercial) fibronectin to ascertain and compare retention of biological activity therein.

The assay required a two-hour incubation period and the target particle was the gelatinized $^{51}$Cr fixed sheep red blood cell. Uptake is expressed as the percent of target particles phagocytized by $2 \times 10^6$ cells and heparin is supplemented in the incubation media. As seen from the table, there is essentially no difference between the intensity of phagocytosis observed in the pasteurized fibronectin of the present invention versus nonpasteurized (commercial) human fibronectin.

Comparison of Fibronectin in the Pasteurized and Non-Pasteurized Form Using the Peritoneal Macrophage Monolayer Assay

| Fibronectin[a] Added (μg) | Pasteurized Net % ID/2 × 10⁶ Cells | Non-Pasteurized Net % ID/2 × 10⁶ Cells |
|---|---|---|
| 10 | 5.97 ± 0.43 | 6.17 ± 0.56 |
| 20 | 7.05 ± 0.39 | 8.47 ± 0.65 |
| 40 | 9.61 ± 0.48 | 11.33 ± 0.94 |
| 80 | 12.45 ± 0.86 | 14.44 ± 0.95 |

[a]Added to a total incubation volume of 1.01 ml. Heparin was added to a dose of 10 units/well. Incutation time was two hours.

It is apparent that numerous modifications and variations of the invention may be made without departing from the spirit and scope thereof. The specific embodiments described are given by way of example only and the invention is limited only by the scope of the appended claims.

What is claimed is:

1. A process for pasteurizing an aqueous solution consisting essentially of fibronectin to inactivate hepatitis viruses therein while preserving its native character consisting essentially of:
   heating and simultaneously mechanically agitating said aqueous solution containing fibronectin at 60° to 70° C. for 10 to 20 hours to effect pasteurization thereof in the presence of: 25% to 50% w/v of a polyol selected from the group consisting of sucrose, maltose, lactose, glucose, mannose, and galactose; 0.01% to 0.5% w/v of a surface active agent selected from the group consisting of sodium cholate, sodium taurocholate, sodium deoxycholate, and sodium glycocholate; and 0.0005 to 0.2M of a chelating agent selected from the group consisting of ethylenediaminetetraacetic acid, ethylene-bis-(oxyethylene nitrile)tetraacetic acid and orthophenanthrolene.

2. A process for pasteurizing an aqueous solution consisting essentially of fibronectin to inactivate hepatitis viruses therein while preserving its native character consisting essentially of:
   heating and simultaneously mechanically agitating said aqueous solution containing fibronectin at 60° to 70° C. 10 to 20 hours to effect pasteurization thereof in the presence of: 25% to 50% w/v of a polyol selected from the group consisting of sucrose, maltose, lactose, glucose, mannose, and galactose; 0.01% to 0.5% w/v of a surface active agent selected from the group consisting of (oxy-1,2-ethanediyl)$_{20}$ monododecanoate sorbitan (oxy-1, 2-ethanediyl)$_{20}$ monohexadecanoate sorbitan, (oxy-1, 2-ethanediyl)$_{20}$ monooctadecanoate sorbitan and (oxy-1, 2-ethanediyl)$_{20}$ mono-9octadecanoate sorbitan; and 0.0005 to 0.2M of a chelating agent selected from the group consisting of ethylenediaminetetraacetic acid, ethylene-bis-(oxyethylene nitrile)tetraacetic acid and orthophenanthrolene.

* * * * *